(12) United States Patent
Mangiardi et al.

(10) Patent No.: US 7,731,654 B2
(45) Date of Patent: Jun. 8, 2010

(54) DELIVERY DEVICE WITH VIEWING WINDOW AND ASSOCIATED METHOD

(75) Inventors: Eric K. Mangiardi, Charlotte, NC (US); Jason M. Reynolds, Charlotte, NC (US); Jeff Reuther, Charlotte, NC (US)

(73) Assignee: Merit Medical Systems, Inc., South Jordan, UT (US)

( * ) Notice: Subject to any disclaimer, the term of this patent is extended or adjusted under 35 U.S.C. 154(b) by 1066 days.

(21) Appl. No.: 11/128,509

(22) Filed: May 13, 2005

(65) Prior Publication Data

US 2006/0258972 A1 Nov. 16, 2006

(51) Int. Cl.
*A61B 1/04* (2006.01)
*A61B 1/00* (2006.01)
*A61F 2/06* (2006.01)

(52) U.S. Cl. .................. 600/130; 600/114; 623/1.11

(58) Field of Classification Search ................. 600/104, 600/105, 130, 137, 114, 140, 164, 170; 623/1.11
See application file for complete search history.

(56) References Cited

U.S. PATENT DOCUMENTS

| | | | |
|---|---|---|---|
| 3,818,511 A | | 6/1974 | Goldberg et al. |
| 3,946,727 A | * | 3/1976 | Okada et al. ............. 600/139 |
| 4,441,215 A | | 4/1984 | Kaster |
| 4,503,569 A | * | 3/1985 | Dotter ..................... 623/1.19 |
| 4,655,771 A | | 4/1987 | Wallsten |
| 4,733,665 A | | 3/1988 | Palmaz |
| 4,743,251 A | | 5/1988 | Barra |
| 4,800,882 A | | 1/1989 | Gianturco |
| 4,820,298 A | | 4/1989 | Leveen et al. |
| 4,856,516 A | | 8/1989 | Hillstead |
| 4,886,062 A | | 12/1989 | Wiktor |

(Continued)

FOREIGN PATENT DOCUMENTS

EP 0 183 372 10/1984

(Continued)

OTHER PUBLICATIONS

PCT Notification of Transmittal of the International Search Report and the Written Opinion of the International Searching Authority, or the Declaration, mailed Jan. 23, 2007 for PCT/US2006/013928 (Filed Apr. 11, 2006).

(Continued)

*Primary Examiner*—Linda C Dvorak
*Assistant Examiner*—Alireza Nia
(74) *Attorney, Agent, or Firm*—Stoel Rives LLP (57) ABSTRACT

A delivery device for positioning and deploying an implantable device within a lumen is provided. The device includes an inner tube positioned within an outer tube and capable of sliding therein, wherein the inner and outer tubes have proximal and distal ends. A side opening is defined in each of the inner and outer tubes, wherein each side opening is defined proximate to the implantable device and is capable of substantially aligning with the other side opening. The device includes an optical device capable of viewing at least a portion of the lumen prior to deploying the implantable device when the side openings are aligned with each other. A mechanism is coupled to at least one of the inner and outer tubes and is operable to deploy the implantable device within the lumen.

32 Claims, 5 Drawing Sheets

U.S. PATENT DOCUMENTS

| | | | |
|---|---|---|---|
| 5,061,275 A | 10/1991 | Wallsten et al. | |
| 5,064,435 A | 11/1991 | Porter | |
| 5,089,005 A | 2/1992 | Harada | |
| 5,102,417 A | 4/1992 | Palmaz | |
| 5,104,404 A | 4/1992 | Wolff | |
| 5,195,984 A | 3/1993 | Schatz | |
| 5,229,431 A | 7/1993 | Pinchuk | |
| 5,292,331 A | 3/1994 | Boneau | |
| 5,383,892 A | 1/1995 | Cardon et al. | |
| 5,383,925 A | 1/1995 | Schmitt | |
| 5,443,498 A | 8/1995 | Fontaine | |
| 5,449,373 A | 9/1995 | Pinchasik et al. | |
| 5,514,154 A | 5/1996 | Lau et al. | |
| 5,534,287 A | 7/1996 | Lukic | |
| 5,540,713 A | 7/1996 | Schnepp-Pesch et al. | |
| 5,562,725 A | 10/1996 | Schmitt et al. | |
| 5,575,818 A | 11/1996 | Pinchuk | |
| 5,591,129 A | 1/1997 | Shoup et al. | |
| 5,591,197 A | 1/1997 | Orth et al. | |
| 5,593,442 A | 1/1997 | Klein | |
| 5,643,312 A | 7/1997 | Fischell et al. | |
| 5,645,559 A | 7/1997 | Hachtman et al. | |
| 5,667,486 A | 9/1997 | Mikulich et al. | |
| 5,674,241 A | 10/1997 | Bley et al. | |
| 5,707,386 A | 1/1998 | Schnepp-Pesch et al. | |
| 5,716,393 A | 2/1998 | Lindenberg et al. | |
| 5,725,572 A | 3/1998 | Lam et al. | |
| 5,733,303 A | 3/1998 | Israel et al. | |
| 5,743,874 A | 4/1998 | Fischell et al. | |
| 5,755,776 A | 5/1998 | Al-Saadon | |
| 5,755,781 A | 5/1998 | Jayaraman | |
| 5,759,192 A | 6/1998 | Saunders | |
| 5,780,807 A | 7/1998 | Saunders | |
| 5,782,838 A * | 7/1998 | Beyar et al. | 623/1.11 |
| 5,803,080 A | 9/1998 | Freitag | |
| 5,807,404 A | 9/1998 | Richter | |
| 5,814,063 A | 9/1998 | Freitag | |
| 5,827,321 A | 10/1998 | Roubin et al. | |
| 5,836,966 A | 11/1998 | St. Germain | |
| 5,843,120 A | 12/1998 | Israel et al. | |
| 5,860,999 A | 1/1999 | Schnepp-Pesch et al. | |
| 5,876,448 A | 3/1999 | Thompson et al. | |
| 5,876,449 A | 3/1999 | Starck et al. | |
| 5,879,370 A | 3/1999 | Fischell et al. | |
| 5,911,732 A | 6/1999 | Hojeibane | |
| 5,922,019 A | 7/1999 | Hankh et al. | |
| 5,922,020 A | 7/1999 | Klein et al. | |
| 5,935,162 A | 8/1999 | Dang | |
| 5,938,682 A | 8/1999 | Hojeibane et al. | |
| 5,947,983 A * | 9/1999 | Solar et al. | 606/144 |
| 5,961,534 A * | 10/1999 | Banik et al. | 606/180 |
| 5,971,950 A | 10/1999 | Lopez et al. | |
| 5,972,018 A | 10/1999 | Israel et al. | |
| 5,980,552 A | 11/1999 | Pinchasik et al. | |
| 5,997,487 A | 12/1999 | Kolehmainen et al. | |
| 6,017,365 A | 1/2000 | Von Oepen | |
| 6,022,371 A | 2/2000 | Killion | |
| 6,027,527 A | 2/2000 | Asano et al. | |
| 6,042,597 A | 3/2000 | Kveen et al. | |
| 6,051,021 A | 4/2000 | Frid | |
| 6,053,941 A | 4/2000 | Lindenberg et al. | |
| 6,059,811 A | 5/2000 | Pinchasik et al. | |
| 6,080,170 A | 6/2000 | Nash et al. | |
| 6,090,136 A | 7/2000 | McDonald et al. | |
| 6,106,548 A | 8/2000 | Roubin et al. | |
| 6,131,266 A | 10/2000 | Saunders | |
| 6,132,461 A | 10/2000 | Thompson | |
| 6,142,931 A * | 11/2000 | Kaji | 600/114 |
| 6,146,403 A | 11/2000 | St. Germain | |
| 6,156,052 A | 12/2000 | Richter et al. | |
| 6,171,334 B1 | 1/2001 | Cox | |
| 6,179,867 B1 | 1/2001 | Cox | |
| 6,183,506 B1 | 2/2001 | Penn et al. | |
| 6,190,353 B1 | 2/2001 | Makower et al. | |
| 6,193,744 B1 | 2/2001 | Ehr et al. | |
| 6,217,608 B1 | 4/2001 | Penn et al. | |
| 6,231,598 B1 | 5/2001 | Berry et al. | |
| 6,251,134 B1 | 6/2001 | Alt et al. | |
| 6,270,524 B1 | 8/2001 | Kim | |
| 6,273,910 B1 | 8/2001 | Limon | |
| 6,277,065 B1 | 8/2001 | Donofrio | |
| 6,283,992 B1 | 9/2001 | Hankh et al. | |
| 6,293,964 B1 | 9/2001 | Yadav | |
| 6,293,966 B1 | 9/2001 | Frantzen | |
| 6,293,968 B1 | 9/2001 | Taheri | |
| 6,299,622 B1 | 10/2001 | Snow et al. | |
| 6,312,459 B1 | 11/2001 | Huang et al. | |
| 6,325,821 B1 | 12/2001 | Gaschino et al. | |
| 6,325,825 B1 | 12/2001 | Kula et al. | |
| 6,336,938 B1 | 1/2002 | Kavteladze et al. | |
| 6,340,364 B2 | 1/2002 | Kanesaka | |
| 6,348,065 B1 | 2/2002 | Brown et al. | |
| 6,352,552 B1 | 3/2002 | Levinson et al. | |
| 6,355,063 B1 | 3/2002 | Calcote | |
| 6,375,676 B1 | 4/2002 | Cox | |
| 6,375,677 B1 | 4/2002 | Penn et al. | |
| 6,409,754 B1 | 6/2002 | Smith et al. | |
| 6,413,269 B1 * | 7/2002 | Bui et al. | 623/1.11 |
| 6,423,084 B1 | 7/2002 | St. Germain | |
| 6,423,091 B1 | 7/2002 | Hojeibane | |
| 6,428,570 B1 | 8/2002 | Globerman | |
| 6,432,133 B1 | 8/2002 | Lau et al. | |
| 6,440,162 B1 | 8/2002 | Cox et al. | |
| 6,443,982 B1 | 9/2002 | Israel et al. | |
| 6,447,525 B2 | 9/2002 | Follmer et al. | |
| 6,451,049 B2 | 9/2002 | Vallana et al. | |
| 6,461,380 B1 | 10/2002 | Cox | |
| 6,461,381 B2 | 10/2002 | Israel et al. | |
| 6,464,687 B1 * | 10/2002 | Ishikawa et al. | 604/891.1 |
| 6,464,720 B2 | 10/2002 | Boatman et al. | |
| 6,464,722 B2 | 10/2002 | Israel et al. | |
| 6,471,721 B1 | 10/2002 | Dang | |
| 6,475,236 B1 | 11/2002 | Roubin et al. | |
| 6,478,815 B1 | 11/2002 | Alt | |
| 6,488,703 B1 | 12/2002 | Kveen et al. | |
| 6,508,834 B1 | 1/2003 | Pinchasik et al. | |
| 6,514,285 B1 | 2/2003 | Pinchasik et al. | |
| 6,524,323 B1 | 2/2003 | Nash et al. | |
| 6,533,805 B1 | 3/2003 | Jervis | |
| 6,533,810 B2 | 3/2003 | Hankh et al. | |
| 6,540,725 B1 * | 4/2003 | Ponzi | 604/272 |
| 6,551,351 B2 | 4/2003 | Smith et al. | |
| 6,562,064 B1 | 5/2003 | deBeer | |
| 6,569,147 B1 | 5/2003 | Evans et al. | |
| 6,569,194 B1 | 5/2003 | Pelton | |
| 6,589,276 B2 | 7/2003 | Pinchasik et al. | |
| 6,592,549 B2 | 7/2003 | Gerdts et al. | |
| 6,599,315 B2 | 7/2003 | Wilson | |
| 6,599,316 B2 | 7/2003 | Vardi et al. | |
| 6,602,285 B1 | 8/2003 | Von Oepen et al. | |
| 6,613,002 B1 | 9/2003 | Clark et al. | |
| 6,613,079 B1 | 9/2003 | Wolinsky et al. | |
| 6,613,080 B1 | 9/2003 | Lootz | |
| 6,613,081 B2 | 9/2003 | Kim et al. | |
| 6,616,688 B2 | 9/2003 | Von Oepen | |
| 6,616,689 B1 | 9/2003 | Ainsworth et al. | |
| 6,616,690 B2 | 9/2003 | Rolando et al. | |
| 6,620,192 B1 | 9/2003 | Jalisi | |
| 6,620,193 B1 | 9/2003 | Lau et al. | |
| 6,620,201 B1 | 9/2003 | Nadal et al. | |
| 6,623,496 B2 | 9/2003 | Snow et al. | |
| 6,623,520 B2 | 9/2003 | Jalisi | |
| 6,635,084 B2 | 10/2003 | Israel et al. | |
| 6,638,300 B1 | 10/2003 | Frantzen | |

| | | |
|---|---|---|
| 6,641,608 B1 | 11/2003 | Pulnev |
| 6,652,546 B1 | 11/2003 | Nash et al. |
| 6,652,572 B2 | 11/2003 | Kugler et al. |
| 6,652,573 B2 | 11/2003 | von Oepen |
| 6,652,579 B1 | 11/2003 | Cox et al. |
| 6,656,201 B2 | 12/2003 | Ferrera et al. |
| 6,656,214 B1 | 12/2003 | Fogarty et al. |
| 6,656,216 B1 | 12/2003 | Hossainy et al. |
| 6,656,220 B1 | 12/2003 | Gomez et al. |
| 6,660,019 B1 | 12/2003 | Richter et al. |
| 6,664,335 B2 | 12/2003 | Krishnan |
| 6,669,723 B2 | 12/2003 | Killion et al. |
| 6,673,106 B2 | 1/2004 | Mitelberg et al. |
| 6,679,911 B2 | 1/2004 | Burgermeister |
| 6,682,536 B2 | 1/2004 | Vardi et al. |
| 6,682,554 B2 | 1/2004 | Oepen et al. |
| 6,689,162 B1 | 2/2004 | Thompson |
| 6,692,483 B2 | 2/2004 | Vardi et al. |
| 6,692,521 B2 | 2/2004 | Pinchasik |
| 6,695,764 B2 * | 2/2004 | Silverman et al. ............ 600/29 |
| 6,699,278 B2 | 3/2004 | Fischell et al. |
| 6,706,061 B1 | 3/2004 | Fischell et al. |
| 6,709,453 B2 | 3/2004 | Pinchasik et al. |
| 6,709,454 B1 | 3/2004 | Cox et al. |
| 6,712,843 B2 | 3/2004 | Elliott |
| 6,712,844 B2 | 3/2004 | Pacetti |
| 6,716,222 B2 * | 4/2004 | McAlister et al. ........... 606/139 |
| 6,716,240 B2 | 4/2004 | Fischell et al. |
| 6,719,782 B1 | 4/2004 | Chuter |
| 6,723,071 B2 | 4/2004 | Gerdts et al. |
| 6,723,118 B1 | 4/2004 | Ballou et al. |
| 6,723,119 B2 | 4/2004 | Pinchasik et al. |
| 6,723,121 B1 | 4/2004 | Zhong |
| 6,730,116 B1 | 5/2004 | Wolinsky et al. |
| 6,730,117 B1 | 5/2004 | Tseng et al. |
| 6,730,120 B2 | 5/2004 | Berg et al. |
| 6,733,524 B2 | 5/2004 | Tseng et al. |
| 6,736,838 B1 | 5/2004 | Richter |
| 6,736,843 B1 | 5/2004 | Fariabi |
| 6,736,844 B1 | 5/2004 | Glatt et al. |
| 6,740,113 B2 | 5/2004 | Vrba |
| 6,740,114 B2 | 5/2004 | Burgermeister |
| 6,740,115 B2 | 5/2004 | Lombardi et al. |
| 6,743,252 B1 | 6/2004 | Bates et al. |
| 6,746,423 B1 | 6/2004 | Wantink |
| 6,746,477 B2 | 6/2004 | Moore |
| 6,746,479 B2 | 6/2004 | Ehr et al. |
| 6,749,629 B1 | 6/2004 | Hong et al. |
| 6,755,856 B2 | 6/2004 | Fierens et al. |
| 6,758,860 B1 | 7/2004 | Penn et al. |
| 6,761,731 B2 | 7/2004 | Majercak |
| 6,764,505 B1 | 7/2004 | Hossainy et al. |
| 6,764,506 B2 | 7/2004 | Roubin et al. |
| 6,764,507 B2 | 7/2004 | Shanley et al. |
| 6,770,088 B1 | 8/2004 | Jang |
| 6,770,089 B1 | 8/2004 | Hong et al. |
| 6,773,445 B2 | 8/2004 | Finlay et al. |
| 6,776,022 B2 | 8/2004 | Kula et al. |
| 6,776,793 B2 | 8/2004 | Brown et al. |
| 6,776,794 B1 | 8/2004 | Hong et al. |
| 6,790,227 B2 | 9/2004 | Burgermeister |
| 6,796,997 B1 | 9/2004 | Penn et al. |
| 6,808,533 B1 | 10/2004 | Goodwin et al. |
| 6,814,749 B2 | 11/2004 | Cox et al. |
| 6,818,013 B2 | 11/2004 | Mitelberg et al. |
| 6,818,014 B2 | 11/2004 | Brown et al. |
| 6,818,015 B2 | 11/2004 | Hankh et al. |
| 6,818,247 B1 | 11/2004 | Chen et al. |
| 6,821,291 B2 | 11/2004 | Bolea et al. |
| 6,821,292 B2 | 11/2004 | Pazienza et al. |
| 6,821,293 B2 | 11/2004 | Pinchasik |
| 6,830,577 B2 | 12/2004 | Nash et al. |
| 6,830,638 B2 | 12/2004 | Boylan et al. |
| 6,833,004 B2 | 12/2004 | Ishii et al. |
| 6,843,797 B2 | 1/2005 | Nash et al. |
| 6,843,802 B1 | 1/2005 | Villalobos et al. |
| 6,849,086 B2 | 2/2005 | Cragg |
| 6,852,124 B2 | 2/2005 | Cox et al. |
| 6,858,037 B2 | 2/2005 | Penn et al. |
| 6,860,898 B2 | 3/2005 | Stack et al. |
| 6,860,900 B2 | 3/2005 | Clerc et al. |
| 6,863,684 B2 | 3/2005 | Kim et al. |
| 6,866,805 B2 | 3/2005 | Hong et al. |
| 6,875,227 B2 | 4/2005 | Yoon |
| 6,878,162 B2 | 4/2005 | Bales et al. |
| 6,881,221 B2 | 4/2005 | Golds |
| 6,881,222 B2 | 4/2005 | White et al. |
| 6,881,223 B2 | 4/2005 | Penn et al. |
| 6,887,264 B2 | 5/2005 | Penn et al. |
| 6,896,696 B2 | 5/2005 | Doran et al. |
| 6,896,697 B1 | 5/2005 | Yip et al. |
| 6,896,698 B2 | 5/2005 | Rolando et al. |
| 6,899,729 B1 | 5/2005 | Cox et al. |
| 6,908,624 B2 | 6/2005 | Hossainy et al. |
| 6,911,041 B1 | 6/2005 | Zscheeg |
| 6,916,336 B2 | 7/2005 | Patel et al. |
| 6,920,677 B2 | 7/2005 | Dolan et al. |
| 6,955,723 B2 | 10/2005 | Pacetti et al. |
| 6,979,348 B2 | 12/2005 | Sundar |
| 7,004,966 B2 | 2/2006 | Edwin et al. |
| 7,172,617 B2 | 2/2007 | Colgan et al. |
| 2002/0038087 A1 * | 3/2002 | Burbank et al. ............. 600/431 |
| 2003/0024534 A1 | 2/2003 | Silvestri et al. |
| 2003/0050686 A1 | 3/2003 | Raeder-Devens et al. |
| 2004/0093056 A1 | 5/2004 | Johnson et al. |
| 2004/0193243 A1 | 9/2004 | Mangiardi et al. |
| 2004/0249433 A1 | 12/2004 | Freitag |
| 2005/0125050 A1 | 6/2005 | Carter et al. |
| 2005/0149160 A1 | 7/2005 | McFerran |

FOREIGN PATENT DOCUMENTS

| | | |
|---|---|---|
| EP | 0 364 420 | 4/1990 |
| EP | 0 540 290 A2 | 10/1991 |
| EP | 0 621 015 A1 | 10/1994 |
| WO | WO 2005/011788 | 2/2005 |

OTHER PUBLICATIONS

U.S. Appl. No. 08/246,320, filed May 19, 1994, Burnmeister et al.

* cited by examiner

DELIVERY DEVICE WITH VIEWING WINDOW AND ASSOCIATED METHOD

BACKGROUND OF THE INVENTION

1) Field of the Invention

The present invention relates to a delivery device and, in more particular, to a delivery device that is capable of being positioned within a lumen and viewing the lumen through a window.

2) Description of Related Art

Stents are devices that are inserted into body lumina such as vessels or passages to keep the lumen open and prevent closure due to a stricture, external compression, or internal obstruction. In particular, stents are commonly used to keep blood vessels open in the coronary arteries, and they are frequently inserted into the ureters to maintain drainage from the kidneys, the bile duct for pancreatic cancer or cholangiocarcinoma, or the esophagus or airways for strictures or cancer. Vascular as well as nonvascular stenting has evolved significantly; unfortunately, there remain significant limitations with respect to effectively implanting the stents into a patient's lumen.

In order to serve its desired function, the stent must be delivered precisely and oriented correctly. Improper installation can lead to tissue luminal inflammation and tissue granulation. In order to facilitate the delivery of stents, delivery devices, such as endoscopes and catheters, have been utilized to deploy stents more precisely. Unfortunately, guidance of the stent has substantially remained a function of physician skill resulting from substantial practice. This fact has become particularly evident with the advent of radially expanding stents. The physician frequently needs to measure the length of the lesion, align a distal end of the of the delivery device, and rely on accurate deployment to ensure that the entire lesion is covered by the stent. Moreover, delivery devices typically do not give physicians adequate visual certainty that the device has been installed at the desired target site. Optical devices are typically employed at a distal end of the delivery device, which provides limited visibility of the entire lesion with respect to the stent. If after full deployment of the stent, the physician discovers the stent has been implanted incorrectly, there is no conventional way of correcting the error short of removing the stent.

Techniques have been developed to address the problem of increasing visibility of the lesion prior to deploying the stent. For example, U.S. Patent Application Publication No. 20040193243 to Mangiardi et al. which is assigned to the present assignee and incorporated herein by reference, discloses a medical appliance optical delivery and deployment apparatus. The apparatus includes an inner tubular member disposed within an outer tubular member, where the outer tubular member is typically shorter than the inner tubular member and movable relative to the inner tubular member. A distal region of the outer tubular member surrounds the stent and maintains the stent in a crimped delivery configuration, while a distal region of the inner tubular member is surrounded by the stent. The outer tubular member may be clear so that the inner tubular member and markers are visible therethrough. An optical guidewire may extend through the inner tubular member or utility channels defined in the outer tubular member to a distal tip, or the distal tip may be configured to have a light source and lens. In addition, the inner tubular member may include optical windows proximate to the distal tip and are preferably beveled and oval to facilitate viewing with an optical instrument. The optical windows may also be staggered along the inner tubular member to increase visualization proximate to the distal tip. Once properly positioned at a site of a lesion, the outer tubular member is retracted to deploy the stent and allow the stent to radially expand.

The inner and outer tubular members, optical instruments, and optical windows provide increased visualization of the lesion prior to deploying the stent. Despite these improvements, additional innovations in positioning an implantable device and visualizing a lesion to promote more accurate delivery of the implantable device are also desired.

Therefore, there is a need in the industry for a delivery device that is capable of effectively and accurately positioning an implantable device within a patient's lumen. In addition, there is a need for a delivery device that is capable of increasing the visibility of the lumen prior to deploying the implantable device.

BRIEF SUMMARY OF THE INVENTION

The invention addresses the above needs and achieves other advantages by providing a delivery device for deploying an implantable device within a lumen. The delivery device includes a side opening in both inner and outer tubes of the device. The side openings in each of the inner and outer tubes align with one another prior to deploying the implantable device within the lumen. An optical instrument, such as a camera, is capable of being positioned proximate to the aligned side openings to view the lumen proximate to a target area. As a result, the delivery device is capable of ensuring that the proximal end of the implantable device is properly positioned proximate to the target area of the lumen.

In one embodiment of the present invention, a delivery device for positioning and deploying an implantable device within a lumen is provided. The device includes a longitudinal outer tube having proximal and distal ends, wherein the implantable device is positioned proximate to the distal end of the outer tube. The device also includes a longitudinal inner tube positioned within the outer tube and having proximal and distal ends, wherein the outer tube is capable of sliding over the inner tube. A side opening is defined in each of the inner and outer tubes, wherein each side opening is defined proximate to the implantable device and is capable of substantially aligning with the other side opening. The device further includes an optical device positioned within the inner tube and proximate to each side opening such that the optical device is capable of viewing at least a portion of the lumen prior to deploying the implantable device when the side openings are aligned with each other. A mechanism is coupled to the inner and/or outer tubes and is operable to deploy the implantable device within the lumen. The mechanism could include at least one actuator coupled to the outer tube.

In various aspects of the delivery device, a coil is positioned within each of the inner and outer tubes, wherein the side opening of each of the inner and outer tubes is defined distally of the respective coils. The side opening of the inner tube may be defined longitudinally between the coil and the implantable device. Each of the inner and outer tubes may include a semi-transparent polymeric material, such as polytetrafluoroethylene and/or polyether block amide. In addition, the optical device is capable of viewing, through the side openings, at least a proximal end of a target area within the lumen. The optical device is also capable of extending through each of the side openings to view a target area within the lumen.

In additional aspects of the delivery device, the device includes a pusher at the distal end of the inner tube and positioned at a proximal end of the implantable device. The side opening of the inner tubular member could be defined proximally of the pusher, and each of the side openings may align with each other proximally of the pusher. Each of the side openings may include an oval having a major and a minor axis, and the major axis of each of the side openings may extend substantially parallel to a longitudinal axis of the respective inner and outer tubes. Furthermore, each of the side openings could extend less than midway about a circumference of each of the inner and outer tubes, and could align with each other proximate to the proximal end of the implantable device.

Another embodiment of the present invention includes a device for viewing a target area within a lumen. The lumen includes a longitudinal inner tube positioned within a longitudinal outer tube, where each of the inner and outer tubes having proximal and distal ends. A side opening is defined in each of the inner and outer tubes, wherein the outer tube is capable of sliding over the inner tube to substantially align each of the side openings with each other. An optical device is positioned within the inner tube and proximate to each side opening such that the optical device is capable of viewing at least a portion of the target area when the side openings are aligned with each other. The device further includes an instrument positioned within the inner tube and capable of performing a procedure while the side openings are aligned. The instrument could perform the procedure through a distal opening defined in each of the inner and outer tubes or through the side openings when the side openings are aligned.

The present invention provides another embodiment of a delivery device for positioning and deploying an implantable device within a lumen. The device includes a longitudinal outer tube having proximal and distal ends, wherein the implantable device is positioned proximate to the distal end of the outer tube. The device also includes a longitudinal inner tube positioned within the outer tube and having proximal and distal ends, wherein the outer tube is capable of sliding over the inner tube. A side opening is defined in each of the inner and outer tubes, wherein each side opening is defined proximate to the implantable device and is capable of substantially aligning with the other side opening prior to deploying the implantable device. A mechanism is coupled to the inner and/or outer tubes and is operable to deploy the implantable device within the lumen. The device could further include an optical device positioned within the inner tube and proximate to each side opening such that the optical device is capable of viewing at least a portion of the lumen when the side openings are aligned with each other.

Furthermore, one aspect of the present invention provides a method for deploying an implantable device within a lumen proximate to a target area. The method includes positioning the implantable device within an outer tube, and sliding the outer tube over an inner tube to substantially align a pair of side openings defined in each of the inner and outer tubes. The method also includes positioning the inner and outer tubes within the lumen, and positioning an optical device within the inner tube and proximate to each of the side openings to view at least a portion of the target area. The method further includes deploying the implantable device with a mechanism proximate to the target area.

In aspects of the method, the positioning step includes positioning the optical device proximate to a proximal end of the target area. The sliding step could also include sliding the outer tube such that the side opening of the outer tube aligns with the side opening of the inner tube proximally of a pusher positioned on a distal end of the inner tube. Furthermore, the deploying step may include sliding the outer tube proximally over the inner tube with the mechanism.

A further embodiment of the present invention provides a method for manufacturing a delivery device. The method includes providing an inner tube and an outer tube, and punching a side opening through a wall in each of the inner and outer tubes. The method also includes attaching a pusher to a distal end of the inner tube, and positioning the inner tube within the outer tube such that each of the side openings is capable of aligning with one another.

Variations of the method include attaching a coil circumferentially and longitudinally within each of the inner and outer tubes. The attaching step could include etching a surface of each of the inner and outer tubes such that the coil attaches to a respective inner and outer tube. The attaching step may include attaching a pusher at a distal end of the inner tube such that the side opening of the inner tube is positioned proximally of the pusher.

BRIEF DESCRIPTION OF THE SEVERAL VIEWS OF THE DRAWINGS

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Figure 1:
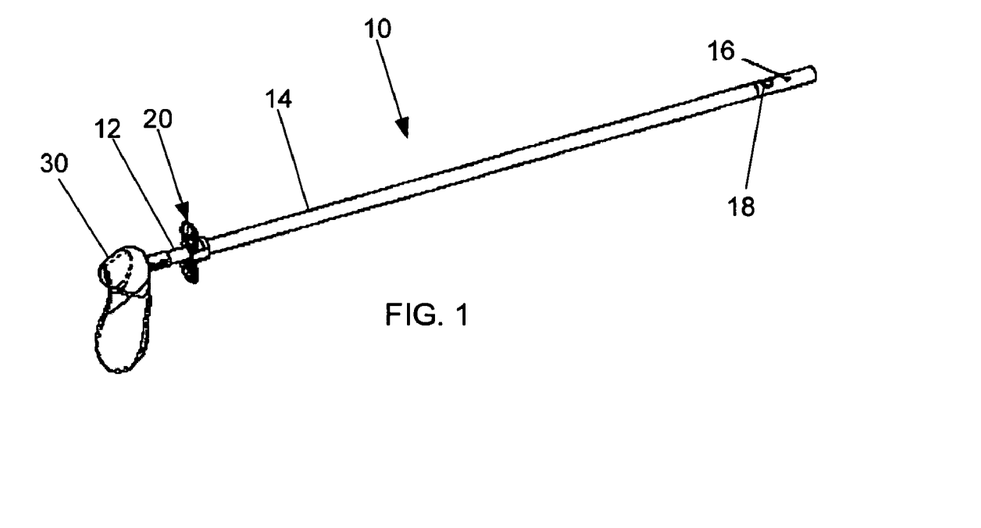
FIG. 1 is a perspective view of a delivery device according to one embodiment of the present invention.

With reference to FIG. 1, a delivery device 10 is shown. The delivery device 10 generally includes an inner tube 12 positioned within an outer tube 14 and capable of sliding therein. The delivery device 10 also includes a deployment mechanism 20 that is capable of deploying an implantable device 16 out of the distal end of the outer tube 14. Side openings 18 are defined in each of the inner 12 and outer 14 tubes. Each of the side openings 18 is capable of aligning with one another such that an optical device 19 may view a target area within a lumen. Therefore, the side openings 18 provide increased visibility of the target area, especially proximal of the target region, to ensure that the implantable device 16 is properly aligned prior to deploying the implantable device within the lumen.

Thus, the delivery device 10 is capable of being deployed within a lumen proximate to a target area. "Target area," as used herein, is not meant to limiting, as the target area, could be a stricture, lesion, tumor, occlusion, fistulae, or other complication where the lumen passageway has been significantly reduced. The delivery device 10 is typically utilized to deploy the implantable device 16 within a lumen. However, the delivery device 10 is also capable of being used for surgical or endoscopic techniques to decrease the complexity of the procedure. For example, the delivery device 10 is also applicable to laparoscopy and arthrectomy.

It is understood that the delivery device 10 is applicable to a wide range of intraluminal applications. For example, the delivery device 10 could be used for implanting an implantable device within lumina of the esophagus, trachea, arteries, or the biliary tract. The implantable device could be, for example, a stent, drug delivery device, or other medical device or drug known to those skilled in the art. Furthermore, any number of configurations of implantable devices 16 could be incorporated and still be within the present scope of the invention. An exemplary embodiment of the interstice geometry of a stent and methods of manufacturing the stent is disclosed in U.S. Patent Publication No. 20040127973, entitled "Removable Biliary Stent," which is assigned to the present assignee and is incorporated herein by reference.

Both the inner tube 12 and outer tube 14 are typically flexible for positioning and maneuvering the tubes within a lumen. Each of the inner 12 and outer 14 tubes are also typically transparent or semi-transparent, such that the inner tube is visible through the outer tube. Moreover, the inner tube 12 may include markers for positioning and deploying the implantable device 16, although the inner and/or outer tubes could include markers if desired. For instance, the distal end of the outer tube 14 may include a marker to locate the distal end of the implantable device 16. The inner tube 12 is slightly smaller in diameter than the outer tube 14 such that the inner tube may slide within the outer tube.

However, the inner 12 and outer 14 tubes may be various sizes and configurations to accommodate a desired implantable device 16. For example, the inner 12 and outer 14 tubes could be about 6 to 10 mm in diameter and about 250-500 mm in length. Each of the inner 12 and outer 14 tubes could also be various diameters and wall thicknesses along the length of each tube for varying flexibility and/or aiding in securing or deploying the implantable device 16. For example, the outer tube 14 could have an incrementally larger diameter from the coil 24 to the distal opening, and could also have a greater wall thickness proximate to the side opening 18.

A substantial portion of each of the inner 12 and outer tubes 14 includes an assembly of polymeric materials and a metal coil 24 formed longitudinally within the polymeric material. For instance, the polymeric materials could be a polytetrafluoroethylene ("PTFE"), such as Teflon® (E.I. DuPont de Nemours and Co. Corp.), and a polyether block amide ("PEBA"), such as Pebax® (Atofina Corp.). Generally, a PTFE liner is placed over a mandrel, and a coil 24 is wound around the PTFE liner while positioned on the mandrel. The PEBA material is configured as a tube and slid over the wound coil 24 and the PTFE liner while the assembly is supported on the mandrel. The assembly is then heated such that the PEBA outer sheath and the PTFE liner are adhered together over the coil to form a tube assembly. The PTFE liner is typically etched so that the PEBA material attaches or fuses to the PTFE material. During the etching process, the PTFE liner is discolored from a clear color to a yellowish brown. Because the PTFE liner is slightly discolored, the side opening 18 provides greater visibility where an optical instrument 19 would be unable to clearly view through the liner itself. The remaining portions of the inner 12 and outer 14 tubes (i.e., the distal portions of the tubes where no coil is present) are typically a combination of PTFE and PEBA materials. The interior of the inner 12 and outer 14 tubes are thus a low-friction PTFE material, which allows various devices and instruments to slide therethrough and requires lower deployment forces when retracting the outer tube 14 during deployment of the implantable device 16. The inner tube 12 is fixedly attached at its proximal end adjacent to the handle 30. Thus, the proximal end of the inner tube 12 may be molded or otherwise attached to a portion of the handle 30, such as with an adhesive.

The coil 24 extends from a proximal end of the each of the inner 12 and outer 14 tubes and within each of the inner and outer tubes proximate to a respective side opening 18. In particular, each coil 24 is positioned proximal of a respective side opening 18. The coils 24 maintain a desired flexibility for the inner 12 and outer 14 tubes, but also preventing kinking or buckling when manipulating the inner and outer tubes within the lumen.

Figure 7:
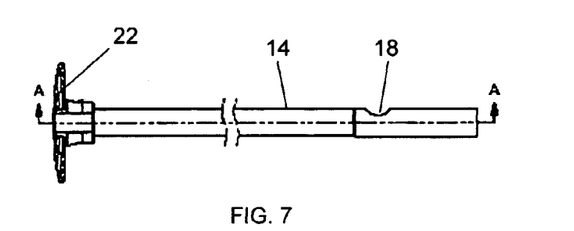
FIG. 7 is a side view of an outer tube assembly according to one embodiment of the present invention.
Figure 8:
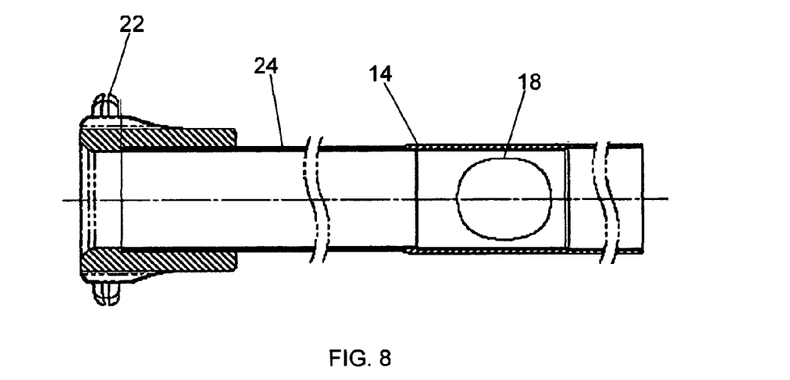
FIG. 8 is a partial cross-sectional view taken through line A-A of the outer tube assembly shown in FIG. 7.
Figure 9:
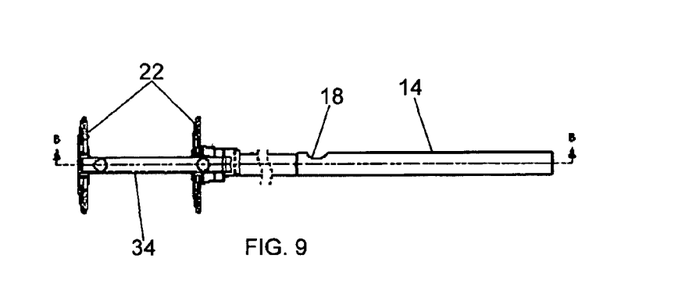
FIG. 9 is a side view of an additional outer tube assembly according to one embodiment of the present invention.
Figure 10:
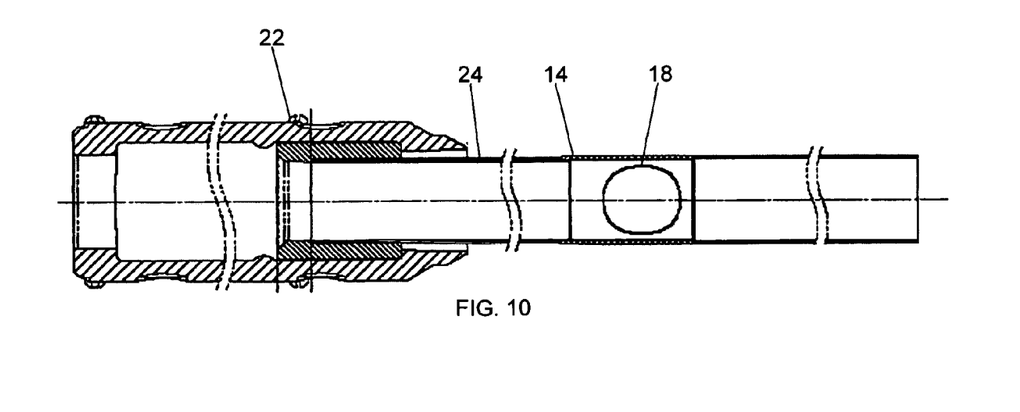
FIG. 10 is a partial cross-sectional view taken through line A-A of the outer tube assembly shown in FIG. 9.

The deployment mechanism 20 typically includes one or more actuators 22 attached to the outer tube 14. Depending on the length of the implantable device 16, there could be one actuator 22 for shorter implantable devices (e.g., 20-60 mm), as depicted in FIGS. 7 and 8, and two or more actuators for longer implantable devices (e.g., 80 mm), as shown in FIGS. 9 and 10. When utilizing two or more actuators 22, the actuators may be operatively connected such that the actuators cooperate to deploy the implantable device 16. For example, FIG. 9 illustrates that a pair of actuators 22 are connected to one another with a connector 34, where one actuator deploys the implantable device 16 partially, while the second actuator deploys the implantable device the remaining distance. The connector 34 is configured such that moving the proximal actuator 22 proximally also causes the distal actuator to move proximally. In addition, the distal actuator 22 may slide within the connector 34 proximally to completely deploy the implantable device 16.

Figure 2A:
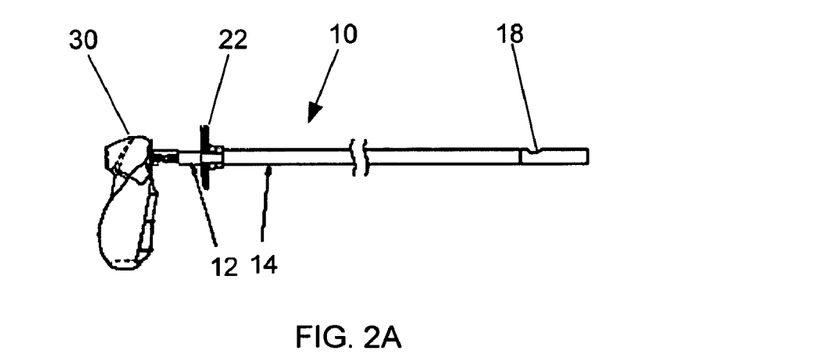
FIG. 2A is a side view of the delivery device shown in FIG. 1.
Figure 2B:
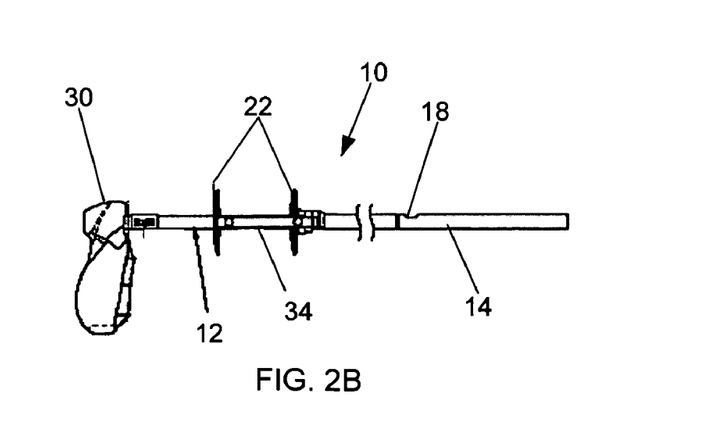
FIG. 2B is a side view of a delivery device according to another embodiment of the present invention.

This arrangement of actuators 22 allows users of the delivery device 10 to deploy the implantable device 16 with one hand if desired. For example, with reference to FIGS. 1 and 2A-B, a user would place a palm of the hand on the handle 30 of the delivery device 10 and extend his or her fingers of the same hand to pull proximally on the actuators 22 in succession. The outer tube 14 is coupled to the actuators 22 such that movement of the actuators causes concurrent sliding of the inner tube 12 within the outer tube 16. More specifically, the proximal end of the outer tube 14 is attached to an actuator 22 such that moving the actuator proximally causes the outer tube 14 to slide proximally over the inner tube 12, while the inner tube remains stationary.

It is understood that the deployment mechanism 20 is not meant to be limiting, as any number of techniques could be employed to deploy the implantable device 16. As such, the deployment mechanism 20 could be any device or actuator capable of deploying the implantable device 16 distally out of the outer tube 14. For example, the actuators 22 could be configured to slide the inner tube 12 distally within the outer tube 14 such that the outer tube remains stationary. Moreover, the mechanism 20 could be any number of sizes and configurations. For instance, although the actuators 22 are T-shaped, the actuators could be configured as a trigger to grip the actuator.

Figure 3:
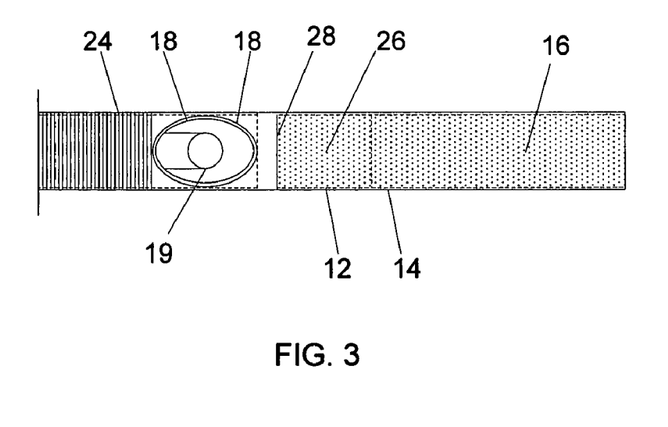
FIG. 3 is a partial plan view of a delivery device, illustrating side windows of inner and outer tubes substantially aligned, according to one embodiment of the present invention.
Figure 5:
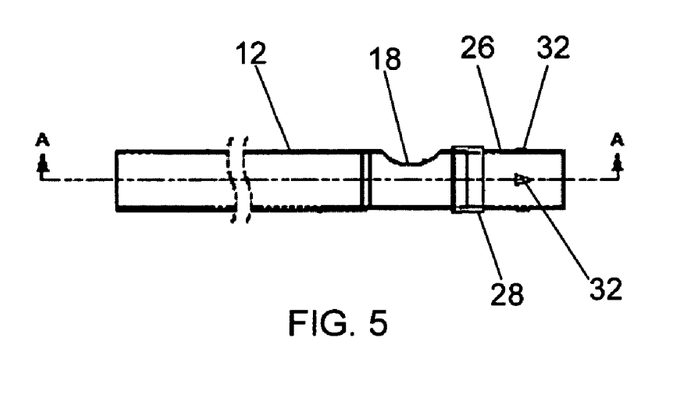
FIG. 5 is a side view of an inner tube assembly according to one embodiment of the present invention.
Figure 6:
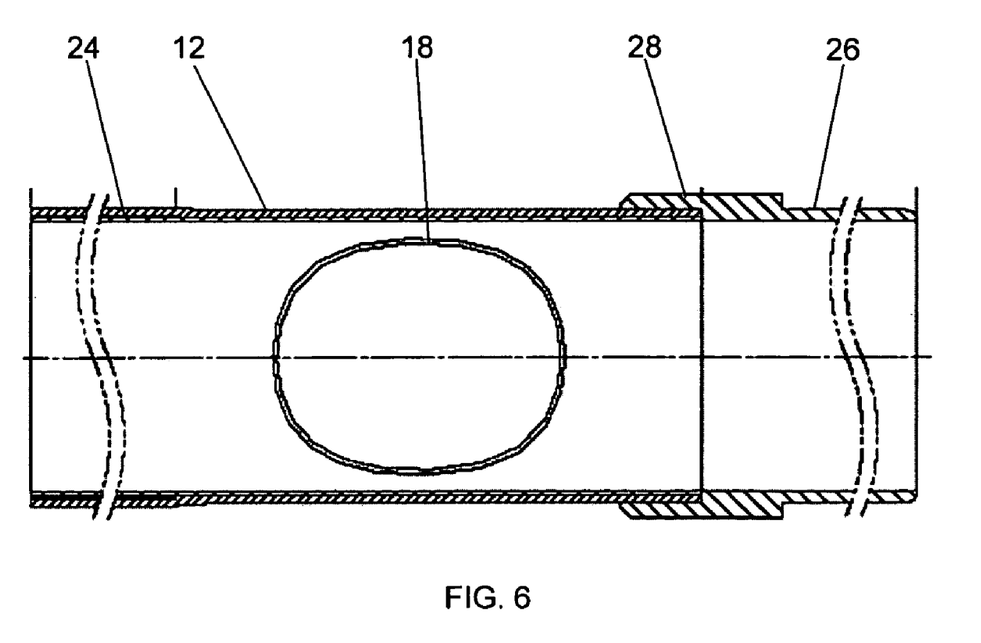
FIG. 6 is a partial cross-sectional view taken through line A-A of the inner tube assembly shown in FIG. 5.

A pusher 26 is attached to a distal end of the inner tube 12. The pusher 26 is positioned at a proximal end of the implantable device 16 when deploying the implantable device. As shown in FIGS. 5 and 6, the inner tube 12 is connected to the pusher 26 with a coupling portion 28 extending from the pusher. The coupling portion 28 is slightly larger in diameter than both the inner tube 12 and the pusher 26. A portion of the inner tube 12 mates within the coupling portion 28 such that the inner tube and pusher 26 are operatively connected. As shown in FIG. 3, when the side openings 18 of each of the inner 12 and outer 14 tubes are aligned, the pusher 26 is positioned distally of the side openings.

A proximal end of the implantable device 16 may extend partially over a portion of the pusher 26. The proximal end of the implantable device 16 could be positioned adjacent to the coupling portion 28, and the coupling portion could be colored or include a marker for identifying the proximal end of the implantable device within the lumen. In addition, the pusher 26 may include anchors 32 that extend outwardly from the pusher at spaced intervals about the circumference of the pusher. The anchors 32 could be barbs, bumps, protuberances, or the like that prevent the implantable device 16 from compressing along its length during deployment of the device. Moreover, the anchors 32 could provide frictional engagement between the inner tube 12, implantable device 16, and outer tube 14, or engage openings defined in the implantable device. The pusher 26 and anchors 32 are also capable of engaging the implantable device 16 to reposition the delivery device 10 or the implantable device when the implantable device is partially deployed. For example, after partially deploying the implantable device 16, the delivery device 10 could be moved proximally to reposition the implantable device within the lumen.

It is understood that the pusher 26 shown and described above is not meant to be limiting, as the pusher may include any number of sizes and configurations in alternative embodiments of the present invention. For instance, the pusher 26 could be integrally formed with the inner tube 12 such that pusher is not a separate component of the inner tube. In addition, the coupling portion 28 could be a separate component than the pusher 26 such that the coupling connects the inner tube 12 and pusher. It is noted that although the term "pusher" is used herein, the pusher 26 does not typically push the implantable device 16. In contrast, the inner tube 12 and pusher 26 remain stationary while the outer tube 14 is retracted. However, the pusher 26 may be configured to advance the implantable device 16 such that the inner tube 12 may be moved distally while the outer tube 14 remains stationary or is moved concurrently in a proximal direction.

With reference to FIG. 3, the side openings 18 of each of the inner 12 and outer 14 tubes are aligned with one another. A gap is provided between the distal end of the pusher 26 and the distal end of the outer tube 14 to accommodate the implantable device 16. The gap allows an optical device 19 to directly view the implantable device 16 for defects or position prior to or during deployment. In addition, because the inner tube 12 stops short of the distal end of the outer tube 14, the optical device 19 is also capable of viewing the target area through the outer tube within the gap.

However, there could be instances where the distal ends of the inner 12 and outer 14 tubes align, such as when a surgical procedure is performed and an implantable device 16 is not required. As such, an optical, surgical, or other instrument is capable of accessing the side openings 18 when aligned with one another. For instance, as shown in FIG. 3, an optical instrument may be positioned within the inner tube 18 and proximate to the opening to view the proximal end of the target area prior to deploying the implantable device 16. Moreover, the optical instrument could be sized and configured to fit through the side openings 18 and view various portions of the target area or the entire target area. The optical, surgical, or other instrument may be any instrument known to those skilled in the art that is capable of accessing the side openings 18 when the side openings are aligned with one another. Thus, the instrument could extend through the distal ends of the inner 12 and outer 14 tubes and/or through the side openings 18. Furthermore, it is understood that although the instrument is typically placed within the lumen of the inner tube 12, the inner tube could include one or more utility channels positioned therein for accommodating various instruments.

Figure 11:
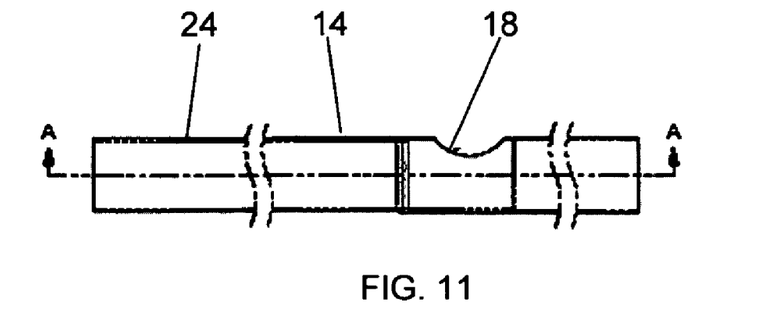
FIG. 11 is side view of an outer tube according to one embodiment of the present invention.
Figure 12:
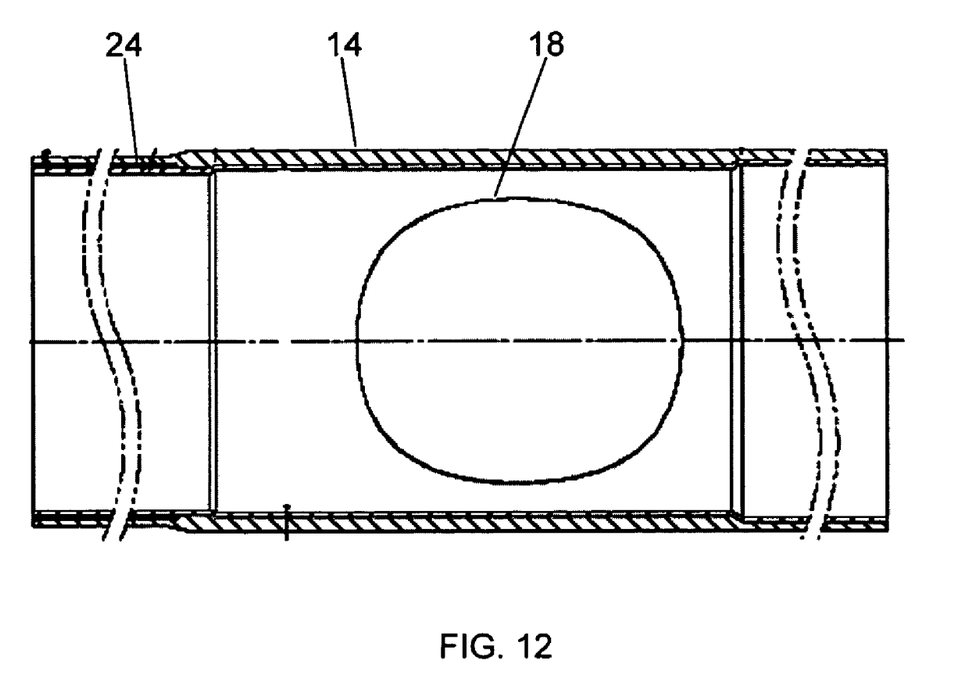
FIG. 12 is a partial cross-sectional view taken through line A-A of the outer tube shown in FIG. 11.

FIGS. 5 and 6 provide further detail regarding the side opening 18 in the inner tube 12, while FIGS. 11 and 12 provide additional details regarding the side opening in the outer tube 14. As shown, the side openings 18 are generally oval in shape and extend less than midway about the circumference of a respective tube. The major axis of the oval side openings 18 extends approximately parallel to the longitudinal axis of the inner 12 and outer 14 tubes, while the minor axis of the side openings extends approximately perpendicular to the longitudinal axis of the inner and outer tubes. The side opening 18 of the inner tube 12 is typically slightly smaller than the outer tube 14. For example, in one aspect of the present invention where the inner tube 12 has a diameter of about 7.5 mm, and the outer tube 14 has a diameter of 8.5 mm, the side openings 18 of each of the inner 12 and outer 14 tubes have about a 5 mm radius (i.e., radius perpendicular to the longitudinal axis of the inner and outer tubes), while the opening of the inner tube is about 7.5 mm in length, and the opening of the outer tube is about 8 mm in length (i.e., length parallel to the longitudinal axis of the inner and outer tubes).

It is understood that the side openings 18 described above should not be limited to any particular size or configuration. For instance, although the side openings 18 are described as being oval, the side openings could be any shape, such as a sphere or polygon. In addition, the side openings 18 could be the same size, or the side opening of the inner tube 12 could be larger than the side opening of the outer tube 14. Moreover, although only a single side opening 18 is shown defined in a respective tube, it is understood that there could be one or more side openings defined in each of the inner 12 and outer 14 tubes and capable of aligning with one another proximate to the target area.

The side openings 18 are typically formed in each of the inner 12 and outer 14 tubes with a punching or similar cutting tool. Because the coil 24 is positioned proximally of the side openings 18, the tool is only required to penetrate the polymeric tubing of the inner 12 and outer 14 tubes. Each side opening 18 would generally be punched separately, although there may be instances where the side openings of both the inner 12 and outer 14 tubes are formed concurrently, such as when the same size of side opening is desired.

The implantable device 16 is deployed within a lumen and proximate to a target area using techniques known to those skilled in the art. For instance, the implantable device may be introduced orally with the delivery device 10, through the lumen, and proximate to a target area. The implantable device 16 is typically contracted to a smaller first diameter from a relaxed position. Once contracted, the implantable device 16 is positioned within the outer tube 14 of the delivery device proximate to the distal end of the outer tube. The inner tube 12 is positioned within the outer tube 14 such that the distal end of the inner tube is positioned proximate to the proximal end of the implantable device 16. A portion of the implantable device 16 may be positioned on the distal end of the inner tube 12 to engage the anchors 32 of the pusher 26. Prior to deployment, the side openings 18 of each of the inner 12 and outer 14 tubes substantially align with one another.

Figure 4:
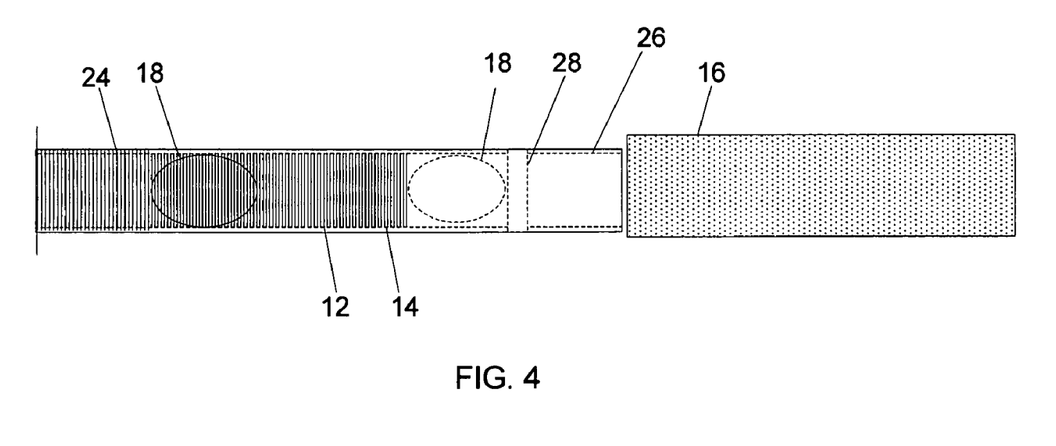
FIG. 4 is another partial plan view of the delivery device shown in FIG. 3, depicting an implantable device deployed from the delivery device.

An optical device 19 is positioned within the inner tube 12 and proximate to a proximal end of the target area and/or implantable device such that the optical device is capable of viewing at least a portion of the target area through the aligned side openings 18. The implantable device 16 is positioned proximate to the target area such that when the implantable device is deployed from the outer tube 14, the implantable device, if formed from an expansible material, can expand to receive the target area and even expand the diameter of the target area. In particular, the distal end of the outer tube 14 is positioned proximate to a distal end of the target area. The outer tube 14 is then retracted over the inner tube 12 using one or more actuators 22, while the pusher 26 supports the proximal end of the implantable device 16. The implantable device 16 is typically deployed incrementally along its length so that a more controlled deployment and accurate position is achieved. FIG. 4 shows the implantable device 16 in a deployed and expanded state, where the pusher 26 is positioned proximate to a distal end of the outer tube 14.

The present invention includes several advantages. For instance, the side openings 18 of the delivery device 10 facilitate increased visibility proximate to the target area. In particular, the optical device 19 is able to view the proximal end of the lesion and/or implantable device to ensure that the implantable device will be deployed to cover the entire target area. Because the implantable device is more accurately positioned within the lumen, the probability of misalignment and subsequent procedures to correct the alignment is reduced. Moreover, the delivery device 10, including the side openings 18, is applicable to a wide range of applications, such as deploying implantable devices and surgical procedures.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A delivery device for positioning and deploying an implantable device within a lumen comprising:
    a longitudinal outer tube having proximal and distal ends, wherein the distal end of the outer tube comprises an opening and the implantable device is positioned proximate to the distal end of the outer tube, wherein the implantable device includes a distal end and a proximal end;
    a longitudinal inner tube positioned within the outer tube and having proximal and distal ends, wherein the outer tube and the inner tube are axially displaceable with respect to one another, and wherein an outer diameter of the distal end of the inner tube is less than an inner diameter of the opening at the distal end of the outer tube;
    a side opening defined in each of the inner and outer tubes, wherein each side opening is defined proximate to the implantable device and is capable of substantially aligning with the other side opening; and
    a mechanism coupled to at least one of the inner and outer tubes and operable to axially displace the inner and outer tubes with respect to one another and to deploy the implantable device out of the opening at the distal end of the outer tube and within the lumen,
    wherein both the inner tube and the outer tube comprise a coil formed longitudinally therein, the coil including proximal and distal ends, positioned within each of the inner and outer tubes having proximal and distal ends, wherein a respective side opening of each of the inner and outer tubes is defined distally of the distal end of each of the respective coils,
    wherein each of the side openings aligns with each other proximate to the proximal end of the implantable device, and wherein the distal end of the outer tube extends distally of the distal end of the inner tube and proximate to the distal end of the implantable device when the side openings are aligned with one another.

2. The delivery device according to claim 1, further comprising an optical device positioned within the inner tube and proximate to each side opening such that the optical device is capable of viewing at least a portion of the lumen prior to deploying the implantable device when the side openings are aligned with each other.

3. The delivery device according to claim 1, wherein the side opening of the inner tube or outer tube including the coil is defined longitudinally between the coil and the implantable device.

4. The delivery device according to claim 3, wherein each of the inner and outer tubes comprises a polymeric material, and wherein each coil is formed within the polymeric material.

5. The delivery device according to claim 4, wherein the polymeric material comprises at least one of a polytetrafluoroethylene and a polyether block amide.

6. The delivery device according to claim 1, wherein each of the side openings comprises an oval having a major and a minor axis.

7. The delivery device according to claim 6, wherein the major axis of each of the side openings extends substantially parallel to a longitudinal axis of the respective inner and outer tubes.

8. The delivery device according to claim 1, wherein each of the side openings extends less than midway about a circumference of each of the inner and outer tubes.

9. The delivery device according to claim 2, wherein the optical device is capable of viewing, through the side openings, at least a proximal end of a target area within the lumen.

10. The delivery device according to claim 2, wherein the optical device is capable of extending through each of the side openings to view a target area within the lumen.

11. The delivery device according to claim 1, further comprising a pusher at the distal end of the inner tube, wherein the implantable device has proximal and distal ends, and wherein the pusher is configured to underlie the proximal end of the implantable device and the distal end of the outer tube extends distally of the pusher and is positioned proximate to the distal end of the implantable device.

12. The delivery device according to claim 11, wherein each of the side openings align with each other proximally of the pusher.

13. The delivery device according to claim 11, wherein the side opening of the inner tube is defined proximally of the pusher.

14. The delivery device according to claim 1, wherein the mechanism comprises at least one actuator coupled to the outer tube.

15. A method for deploying an implantable device within a lumen proximate to a target area comprising:
   an implantable device having a proximal end and a distal end;
   positioning the implantable device within an outer tube, wherein the outer tube has an open distal end;
   sliding the outer tube over an inner tube to substantially align a pair of side openings defined in each of the inner and outer tubes;
   positioning the inner and outer tubes within the lumen;
   viewing at least a portion of the target area proximate to each of the side openings; and
   deploying the implantable device out of the open distal end of the outer tube and proximate to the target area such that the implantable device expands as the inner and outer tubes are displaced with respect to one another;
   wherein both the inner tube and the outer tube comprise a coil formed longitudinally therein, the coil including proximal and distal ends, positioned within each of the inner and outer tubes having proximal and distal ends, wherein a respective side opening of each of the inner and outer tubes is defined distally of the distal end of each of the respective coils,
   wherein each of the side openings aligns with each other proximate to the proximal end of the implantable device, and wherein the distal end of the outer tube extends distally of the distal end of the inner tube and proximate to a distal end of the implantable device when the side openings are aligned with one another.

16. The method according to claim 15, wherein viewing comprises positioning an optical device within the inner tube and proximate to a proximal end of the target area.

17. The method according to claim 15, wherein sliding comprises sliding the outer tube such that the side opening of the outer tube aligns with the side opening of the inner tube proximally of a pusher positioned on a distal end of the inner tube.

18. The method according to claim 15, wherein deploying comprises retracting the outer tube proximally over the inner tube such that the distal end of the outer tube is moved from a position offset from a distal end of the inner tube prior to deploying the implantable device to a position substantially aligned with the distal end of the inner tube when the implantable device is fully deployed within the lumen.

19. A delivery device for positioning and deploying an implantable device within a lumen comprising:
   an implantable device having proximal and distal ends; a longitudinal outer tube having proximal and distal ends and a lumen extending therebetween, wherein the distal end of the outer tube is open and the implantable device is positioned within the lumen of the outer tube and proximate to the distal end of the outer tube;
   a longitudinal inner tube positioned within the outer tube and having proximal and distal ends, wherein the outer tube and the inner tube are axially displaceable with respect to one another;
   a side opening defined in each of the inner and outer tubes, wherein each side opening is defined proximate to the implantable device and is capable of substantially aligning with the other side opening prior to deploying the implantable device; and
   a mechanism coupled to at least one of the inner and outer tubes and operable to axially displace the inner and outer tubes with respect to one another such that the implantable device is configured to expand out of the open distal end of the outer tube and within the lumen as the inner and outer tubes are axially displaced with respect to one another,
   wherein both the inner tube and the outer tube comprise a coil formed longitudinally therein, the coil including proximal and distal ends, positioned within each of the inner and outer tubes having proximal and distal ends, wherein a respective side opening of each of the inner and outer tubes is defined distally of the distal end of each of the respective coils,
   wherein each of the side openings aligns with each other proximate to the proximal end of the implantable device, and wherein the distal end of the outer tube extends distally of the distal end of the inner tube and proximate to a distal end of the implantable device when the side openings are aligned with one another.

20. The device according to claim 19, further comprising an optical device positioned within the inner tube and proximate to each side opening such that the optical device is capable of viewing at least a portion of the lumen when the side openings are aligned with each other.

21. The device according to claim 19, further comprising a pusher at the distal end of the inner tube, wherein the pusher is configured to underlie the proximal end of the implantable device and the distal end of the outer tube extends distally of the pusher and is positioned proximate to the distal end of the implantable device.

22. The delivery device according to claim 21, wherein each of the side openings align with each other proximally of the pusher.

23. The delivery device according to claim 21, wherein the side opening of the inner tubular member is defined proximally of the pusher.

24. The delivery device according to claim 21, wherein the side opening of the inner tube or the outer tube including the coil is defined longitudinally between the coil and the implantable device.

25. The device according to claim 19, wherein an outer diameter of the distal end of the inner tube is less than an inner diameter of the open distal end of the outer tube.

26. The device according to claim 19, wherein the implantable device comprises a self-expanding stent and is configured to lie adjacent to the lumen of the outer tube.

27. The device according to claim 1, wherein the mechanism is configured to retract the outer tube relative to the inner tube such that the distal end of the inner tube is adjacent to the opening at the distal end of the outer tube when the implantable device is deployed.

28. The delivery device according to claim 21, wherein the inner tube and the outer tube comprise a polymeric material, and wherein each coil is formed within the polymeric material.

29. The delivery device according to claim 15, wherein sliding comprises sliding the inner and outer tubes such that a coil formed within either the inner tube or the outer tube is located proximally of the side opening of the outer or inner tube, respectively.

30. The delivery device according to claim 29 wherein sliding comprises sliding the inner and outer tubes such that a coil formed within the inner tube is located proximally of the side opening of the outer tube and a coil formed within the outer tube is located proximally of the side opening of the inner tube.

31. A delivery device for positioning and deploying an implantable device within a lumen comprising:

- a longitudinal outer tube having proximal and distal ends, wherein the implantable device is positioned within the outer tube, wherein the implantable device includes a proximal end and a distal end, and wherein the outer tube comprises a coil formed longitudinally therein;
- a longitudinal inner tube positioned within the outer tube and having proximal and distal ends, wherein the outer tube and the inner tube are axially displaceable with respect to one another, and wherein the inner tube comprises a coil formed longitudinally therein;
- a side opening defined in each of the inner and outer tubes, wherein each side opening is defined proximate to the proximal end of the implantable device and is capable of substantially aligning with the other side opening, and wherein each side opening is defined proximally of a respective coil formed in each of the inner and outer tubes; and
- a mechanism coupled to at least one of the inner and outer tubes and operable to axially displace the inner and outer tubes with respect to one another to deploy the implantable device within the lumen.

32. A delivery device for positioning and deploying an implantable device within a lumen comprising:

- a longitudinal outer tube having proximal and distal ends, wherein the implantable device, having a proximal end and a distal end, is positioned within the outer tube;
- a longitudinal inner tube positioned within the outer tube and having proximal and distal ends, wherein the outer tube and the inner tube are axially displaceable with respect to one another;
- a side opening defined in each of the inner and outer tubes, wherein each side opening is defined proximate to implantable device and is capable of substantially aligning with the other side opening, and wherein the distal end of the outer tube extends distally of the distal end of the inner tube a distance approximately equal to a length of the implantable device when the side openings are aligned with one another; and
- a mechanism coupled to at least one of the inner and outer tubes and operable to axially displace the inner and outer tubes with respect to one another to deploy the implantable device within the lumen, and wherein both the inner tube and the outer tube comprise a coil formed longitudinally therein, the coil including proximal and distal ends, positioned within each of the inner and outer tubes having proximal and distal ends, wherein a respective side opening of each of the inner and outer tubes is defined distally of the distal end of each of the respective coils, wherein each of the side openings aligns with each other proximate to the proximal end of the implantable device, and wherein the distal end of the outer tube extends distally of the distal end of the inner tube and proximate to a distal end of the implantable device when the side openings are aligned with one another.

* * * * *